(12) United States Patent
Armonti et al.

(10) Patent No.: US 7,001,612 B2
(45) Date of Patent: Feb. 21, 2006

(54) COMPOSITION FOR THE RELIEF OF HEAT STRESS

(75) Inventors: Fausto Armonti, Bibbiano (IT); Donato Mitola, Abano Terme (IT); Jacobus C. Samson, Selvazzano (IT)

(73) Assignee: All Sun HSF Company Limited, Montreal (CA)

( * ) Notice: Subject to any disclaimer, the term of this patent is extended or adjusted under 35 U.S.C. 154(b) by 0 days.

(21) Appl. No.: 10/074,847

(22) Filed: Feb. 13, 2002

(65) Prior Publication Data

US 2002/0102313 A1 Aug. 1, 2002

Related U.S. Application Data

(63) Continuation of application No. 09/486,494, filed as application No. PCT/EP98/05422 on Aug. 26, 1998.

(51) Int. Cl.
*A61K 47/00* (2006.01)

(52) U.S. Cl. .............. 424/439; 424/641; 424/677; 424/639; 426/74; 426/569; 426/590; 426/648; 426/649; 426/658; 514/251; 514/276; 514/458; 514/474

(58) Field of Classification Search ............ 424/439, 424/639, 641, 677; 426/74, 569, 590, 648, 426/649, 658; 514/251, 276, 458, 474
See application file for complete search history.

(56) References Cited

U.S. PATENT DOCUMENTS

| | | | |
|---|---|---|---|
| 3,894,148 A | 7/1975 | Ecker | 424/180 |
| 4,042,684 A | 8/1977 | Kahm | 726/74 |
| 4,309,417 A | 1/1982 | Staples | 424/128 |
| 4,322,407 A | 3/1982 | Ko | 424/128 |
| 4,448,770 A | 5/1984 | Epting, Jr. | 424/153 |
| 4,592,909 A | 6/1986 | Winer et al. | 424/127 |
| 4,725,427 A | 2/1988 | Ashmead et al. | 424/44 |
| 4,738,856 A | 4/1988 | Clark | 426/77 |
| 4,874,606 A | 10/1989 | Boyle et al. | 514/53 |
| 4,981,687 A | 1/1991 | Fregly et al. | 424/439 |
| 5,032,411 A | 7/1991 | Stray-Gundersen | 428/74 |
| 5,089,477 A | 2/1992 | Fregly et al. | 514/23 |
| 5,114,723 A | 5/1992 | Stray-Gundersen | 426/74 |
| 5,147,650 A | 9/1992 | Fregly et al. | 424/439 |
| 5,236,712 A | 8/1993 | Fregly et al. | 424/439 |
| 5,270,297 A | 12/1993 | Paul et al. | 514/23 |
| 5,292,538 A | 3/1994 | Paul et al. | 426/74 |
| 5,294,606 A | 3/1994 | Hastings | 514/53 |
| 5,334,408 A * | 8/1994 | Brule et al. | 426/57 |
| 5,536,506 A | 7/1996 | Majeed et al. | 424/464 |
| 5,587,179 A | 12/1996 | Gergely et al. | 424/466 |
| 5,626,884 A | 5/1997 | Lockett | 424/639 |

FOREIGN PATENT DOCUMENTS

| | | |
|---|---|---|
| CN | 1 104 457 | 7/1995 |
| DE | 4 320 853 | 5/1995 |
| EP | 0 387 042 | 9/1990 |
| EP | 587 972 | 3/1994 |
| RU | 1 192 187 | 6/1994 |
| WO | WO 92/15206 | 9/1992 |

OTHER PUBLICATIONS

Seutter, et al., The Quantitative Analysis of Some Constituents of Crude Sweat, *Dermatologica* 141:226-233, 1970.
Fukumoto, T., et al., "Differences in Composition of Sweat Induced by Thermal Exposure and by Running Exercise", *Clin. Cardiol.*, vol. 11, pp. 707-709 (1988).

* cited by examiner

*Primary Examiner*—Thurman K. Page
*Assistant Examiner*—Lakshmi Channavajjala
(74) *Attorney, Agent, or Firm*—Flynn, Thiel, Boutell & Tanis, P.C.

(57) ABSTRACT

A composition for the relief of heat stress, particularly for restoration of electrolyte balance due to passive exposure to heat resulting in excessive transpiration/perspiration, without strenuous physical activity, contains predetermined levels of selected electrolytes including, in part by weight, sodium ion not exceeding 250 parts, at least 100 parts of potassium ion, at least 100 parts of magnesium ion, and carbohydrates not exceeding 2.5% by weight, as needed for organoleptic purposes only. The composition can further include up to 30 parts of zinc, up to 10 parts of manganese, and from 65 to 400 parts of calcium. Furthermore, the composition can contain oligoelements, dermoprotective vitamins and anti-oxidants so as to compensate for the chemical changes which might occur in the skin of a person passively exposed to heat.

10 Claims, No Drawings

COMPOSITION FOR THE RELIEF OF HEAT STRESS

This is a continuation of Ser. No. 09/486,494, filed May 17, 2000 under 35 U.S.C. 371, which represents the national stage of International Application No. PCT/EP98/05422 filed Aug. 26, 1998, which claims priority from U.S. application Ser. No. 08/924,858 filed Aug. 30, 1997.

FIELD OF THE INVENTION

The invention relates to a composition for the relief of heat stress. In particular, the invention relates to a composition for restoration of electrolyte balance due to sweating in the absence of strenuous physical exertion.

BACKGROUND OF THE INVENTION

Generally, it has been recognized that vigorous activities such as sports and exercising result in the loss of salt and other minerals through sweating. The production of eccrine transpiration is the physiological mechanism to eliminate excess heat from the human body by fluid evaporation on the skin. According to environmental conditions and physical exercise, daily fluid losses of up to 3 liters may occur. In such conditions, one tends to compensate these fluid losses, through a physiological thirst mechanism, by the intake of sufficient fluid.

It has been established that along with eccrine transpiration, significant amounts of electrolytes are eliminated, which may account for systemic losses of up to 75 mEq of Na+ and Cl−, 60 mEq of K+ and Ca++, and 10 mEq of $HCO_3-$ (Seutter et al., *The Quantitative Analysis of Some Constituents of Crude Sweat*, Dermatolgica 141:226–233, 1970; Cage et al., *Eccrine Glands* in Dermatology in General Medicine, Fitzpatrick et al., McGraw-Hill, pp. 691–704, 1987). That such electrolyte losses may have negative consequences for the normal function of the human body has since long been recognized. The electrolyte losses consequent to excessive sweating, for instance in athletes, may contribute to early exhaustion, fatigue, muscle cramps, cardiac effects (arrhythmias) and CNS effects (asthenia). For this reason rational compositions have been successfully developed to reintegrate electrolyte losses by means of suitable rehydration beverages.

As far as reintegration of electrolyte losses in sportsmen is concerned, many compositions, particularly beverages are known which both rehydrate and provide energy to combat fatigue and stress. These compositions are specifically intended for people engaging in physical exercise, to improve performance and endurance. by supplying various sources of carbohydrates, along with selected mineral electrolytes.

For example, U.S. Pat. No. 5,292,538 (Paul et al.) describes a nutritional anabolic composition capable of providing for sustained energy as needed for strenuous physical exertion causing fatigue. This composition is essentially an energy formula in which carbohydrates play the foremost role. The characteristic feature of this composition lies in the particular combination of carbohydrate sources with partially hydrolyzed protein and magnesium in the form of an amino acid chelate. Additional electrolytes and vitamins play a subordinate role in achieving the objective of providing sustained energy and anabolic nutrition.

Like the above document, U.S. Pat. No. 5,270.297 (Paul et al.) describes a nutritional anabolic composition capable of providing for sustained energy as needed for strenuous physical exertion causing fatigue, with the additional objective of maintaining and/or enhancing the hydration state, besides the endurance, in conditions of physical stress, which is referred to physical exercise. The compositions claimed are centered on carbohydrate sources, and include amino acid chelates of sodium, calcium, potassium and manganese. It is to be noted that sodium levels of this composition are very high, like any other rehydration and energy formula for use in sports which the Inventors are aware of.

U.S. Pat. Nos. 5,032,411 and 5,114,723 (Stray-Gundersen) describe hypotonic beverage compositions intended for the intake by people engaging in physical activity, particularly in the heat, who have an increased metabolic demand and are in need of rehydration. The characteristic feature of these composition lies in the accurate definition of the osmolarity level to promote rapid absorption of the carbohydrate sources supplied in the beverage. The essential aspect of the compositions lies in the particular combination of carbohydrate sources with iron and other electrolytes.

U.S. Pat. No. 5,294,606 (Hastings) is directed to an isotonic energy composition, based on various carbohydrates along with the mineral electrolytes used for rehydration of sportsmen. The composition also contains chromium. U.S. Pat. No. 4,322,407 (Ko) describes an electrolyte drink intended for physical recovery after strenuous exercise. It supplies a high level of carbohydrate energy sources, along with mineral electrolytes used for rehydration of sportsmen and vitamin C. U.S. Pat. No. 4,874,606 (Boyle et al.) refers to a rapidly hydrating beverage for use by people engaging in medium to heavy levels of exercise. This beverage essentially supplies carbohydrate, sodium chloride, citrate and a specific compound (L-aspartyl-L-phenyl-alanine methyl ester) claimed to increase the rate of gastric emptying. It does not supply other electrolytes, oligoelements or vitamins. U.S. Pat. No. 4,309,417 (Staples) describes a beverage composition intended for the rapid replacement of body fluids, proteins and electrolytes lost during periods of strenuous physical activity. This composition is essentially directed to the use of whey protein concentrate as an energy source, besides the usual carbohydrates. It contains a high level of sodium, needed to achieve isotonicity of the solution, and the oligoelements naturally deriving from the whey protein. U.S. Pat. No. 3,894,148 (Ecker) is directed to a method for enhancing the energy metabolism of sportsmen, by administering fructose, used in conjunction with an electrolyte mix of sodium and potassium ions, as chlorides and as phosphates. The objective is to avoid the oxygen debt, causing build-up of lactic acid in athletes' muscles. U.S. Pat. No. 4,042,684 (Kahm) describes a dietetic beverage intended to supply carbohydrate and electrolytes to subjects engaging in vigorous physical activity, including hot and/or humid environments. The beverage only supplies, along with the sugars, sodium and potassium electrolytes. U.S. Pat. No. 4,448,770 (Epting) refers to a dietetic beverage for consumption by people needing fluid and electrolyte replacement during periods of exercise or potassium deficiency. This includes athletes and other people in conditions where fluid and/or potassium loss is a result of strenuous physical or mental activity, illness or side-effects of drugs. The beverage is essentially free of sodium ions, but supplies, besides sugar, very high levels of potassium, calcium and magnesium. U.S. Pat. No. 4,981,687 (Fregly et al.) describes a method and composition to improve physiological responses to exercise and exposure to sunlight and heat. The method to combat these effects is based on the administration of glycerol or pyruvate, besides the usual carbohydrate sources. It is to be noted that the beneficial action is based on a fluid retention effect. Subsequent patents released to the same authors (U.S. Pat. Nos. 5,147,650 and 5,236,712) extend such compositions to include lactate and alanine.

Beside rehydrating beverages or compositions for use in connection with physical exercise, often under strenuous conditions, other compositions are known from the prior art which pursue medical or pharmaceutical objectives.

For example, U.S. Pat. No. 5,626,884 (Lockett) describes a maintenance formula for patients suffering sickle cell disease, a genetically determined pathological modification of blood oxygenation. This document teaches a method of treating the above disease state of red blood cells by administering a very extensive cocktail of commonly known nutritional compounds. It is particularly important to note that this composition does not include sodium ions, which may be possibly present only in traces.

Other examples of medical compositions or processes for the preparation thereof include U.S. Pat. No. 4,725,427 (Ashmead et al.) which describes a technological process for the preparation of effervescent mineral granules, to be dissolved in water to yield a carbonated drink, supplying different ranges of vitamins and minerals in the form of amino chelates. The objective of this preparation is to improve the bioavailability of multivitamin mineral supplements in general, without any specific intended purpose. Further, U.S. Pat. No. 4,738,856 (Clark) describes a method to yield a beverage formulation intended for nutritional calcium supplementation, along with magnesium and potassium, in the form of readily absorbed organic salts. This beverage composition is intended to lower blood pressure, reduce blood alcohol, as well as supplying the recommended daily allowance of calcium, especially for post-menopausal women. U.S. Pat. No. 5,587,179 (Gergely et al.) is directed to a process for the manufacture of pharmaceutical formulations as effervescent or disintegrating tablets, with exemplifying reference to the administration of loperamide for the treatment of diarrhea. The mineral salts included have the significance of providing for the effervescent effect, combined with the compensation of electrolyte losses at the intestinal level. U.S. Pat. No. 5,536,506 (Majeed et al.) refers to the use of a natural alkaloid (piperine, in therapeutically effective amounts) to increase the gastrointestinal absorption, bioavailability and/or the metabolic utilization of diverse nutritional compounds, including many vegetal compounds, most vitamins, amino acids, and minerals. Also topical and intravenous administration is disclosed.

The Inventors have been involved in the problem that such beverages, widely used today for rehydration purposes in sportsmen, not to mention those pharmaceutical compositions specifically directed to treat specific diseases, appeared to be inappropriate for the support of transpiration problems in people undergoing thermal therapy such as hot mud applications.

Thermal treatment is widely used in Europe mainly for various types of musculoskeletal pathologies, which are reported to benefit significantly from the application of external heat. During a typical treatment session with thermal mud application, patients may lose up to two liters of transpiration, and consequently suffer avid thirst during and after the treatment sessions.

It is well known to the medical supervisors that these treatment consequences need accurate monitoring and adequate prevention, since if left untreated, severe sequelae may follow, in terms of the feared "thermal crisis", associated with significant electrolyte imbalance, impairing cell function and causing systemic adverse effects, pathophysiologically similar to heat shock. In more general terms, thermal therapy induces a high level of "heat stress".

The inventors found that the thermal therapy establishments determined that the rehydration beverages developed for sports purposes were not fit for their patients. First of all, these drinks generally contain a significant energy source, mostly in the form of readily absorbed and metabolized carbohydrates such as glucose. The great majority of patients undergoing thermal therapy are typically on a diet, because weight loss is a secondary benefit pursued by most patients applying for thermal therapy. Furthermore there is a high incidence of type II diabetes among these patients, most being elderly.

Apart from this obvious preoccupation on the carbohydrate component, the Inventors surmised that there could be significant physiological differences between the rehydration needs of young sportsmen and those of middle-aged and elderly people passively undergoing therapeutic heat application. It had indeed been reported by Fukumoto et al. in *Differences in Composition of Sweat Induced by Thermal Exposure and by Running Exercise*, Clinical Cardiology 11:707–709, (1988) that the composition of sweat differed significantly between volunteers when engaged in strenuous physical activity, and the same volunteers when submitting passively to environmental heat. They reported that during the passive heat conditions much lower amounts of sodium and chloride ions were found in the collected sweat samples than in the physical exercise conditions, whereas the levels of potassium ions were found to be comparable in both conditions.

On this basis, an investigation was made of the specific rehydration needs in passive heat conditions, such as applied during thermal therapy, in order to devise a physiologically appropriate nutritional support useful to reintegrate electrolyte losses in these conditions and to give suitable support for skin physiology. It had indeed been noted incidentally that patients' skin often appeared to suffer after repeated application of external heat, by means of thermal mud baths, showing signs of accelerated ageing, especially when associated with massive sunlight of UV exposure, often practiced in the Italian health spas.

More in general, there is thus a need for a composition suited for a person who sweats under conditions not associated with strenuous activities, such as passive heating or hyphen sweating, to compensate for the specific chemical imbalance arising from the sweating and further preferably to compensate for the biochemical changes which might occur in the person's skin. Such a composition preferably should be suited to be taken either before or after sweating.

The Inventors also found that rehydration needs of the patients subjected to thermal therapies are comparable to those of healthy people normally subjected to prolonged exposure to environmental heat and sunshine, especially in the absence of strenuous physical activity. Contrary to common beliefs, it has been found that the rehydration beverages developed for sports purposes are not fit for people in the above conditions. On the other side, it is simply not possible to think of providing a pharmaceutical composition to healthy people not subjected to medical supervision. A further problem which lies with providing healthy people with the majority of beverages of the known art is that assumption of carbohydrate components or sugar is contrary to the idea of getting or keeping a slim line, which is instead the aim of many.

It is therefore an object of the present invention to provide a composition for rehydration and restoration of electrolyte balance, which may prove useful in avoiding or ameliorating the adverse physiological effects which can result from prolonged exposure to environmental heath and sunshine, specifically in the absence of strenuous physical activity.

It is another object of the present invention to provide a composition of the type mentioned above which includes a correct amount of electrolytes to combat passive exposure to heat resulting in excessive transpiration/perspiration, without however providing a, high level of calories.

It is a further object of the present invention to provide a composition which is adapted to be provided in the form of a beverage, powder, solid items such as tablets and the like, and even in a frozen state.

SUMMARY OF THE INVENTION

The above objects are achieved by means of a composition useful for the relief of heat stress, including selective restoration of the potassium and magnesium ion, systemic decreases of which are associated with passive exposure to heat/sun and resultant intensive transpiration/perspiration, the composition comprising, when solubilized, at least 100 parts in weight of potassium ion; sodium ion not exceeding 250 parts in weight; at least 100 parts in weight of magnesium ion; and a carbohydrate source not exceeding 2.5% by weight for organoleptic purposes only. While the sodium level, although low, is greater than zero, carbohydrates are however needed for organoleptic purposes only and their level is to a certain extent non-critical so that it might reach a zero value.

The above composition may also additionally comprise up to 30 parts of zinc, up to 10 parts of manganese; from 65 to 400 parts of calcium; and also oligoelements, dermoprotective vitamins and anti-oxidants so as to compensate for the biochemical changes which might occur in the skin of a person passively exposed to heath and/or sunshine. In particular, the oligoelements, dermoprotective vitamins and anti-oxidants are selected in the group comprising: from 2.5 to 250 parts of rutin, from 0.04 to 0.3 parts of biotin, from 15 to 120 parts of vitamin C, from 4 to 30 parts of beta-carotene, and from 2.5 to 20 parts of vitamin E.

The composition may be prepared in the form of a powder, in a solid form or in liquid form, solubilized in water. In this latter case, the water solution comprising the composition may be in the frozen state.

When solubilized in water, the composition may provide a hypocaloric beverage, wherein for each liter of beverage each part by weight of composition corresponds to 1 mg. In this hypocaloric beverage, the amount of carbohydrates, when present, contributes for no more than 120 kcal per liter of beverage.

In one preferred, although non limiting embodiment of the invention to be used in the form of a beverage, the composition comprises from about 0.3 to about 0.7 g/liter of a sodium compound; from about 0.3 about 0.5 g/liter of a potassium compound; from about 1.2 to about 1.8 g/liter of a magnesium compound; from about 0.2 to about 0.8 g/liter of a calcium compound; from about 0.002 to about 0.005 g/liter of a manganese compound; from about 0.04 g/liter to about 0.08 g/liter of a zinc compound; from about 0.025 to about 0.25 g/liter of Rutin; from about 0.00013 to about 0.0003 g/liter of Biotin; from about 0.004 to about 0.03 g/liter of beta-carotene; and from about 0.005 to about 0.02 g/liter of alpha-tocopherol.

The composition according to the invention can be utilized for electrolyte replacement for certain sports which involve exposure to the summer heat and UV but not necessarily demanding physical activities such as sports fishing, horseback riding, golf playing, mountain hiking, sailing and boating.

The composition according to the invention can be utilized for electrolyte replacement for people who may work in hot environments such as professional cooks, truck drivers, train drivers, and the like.

Although the composition of the present invention is not to be construed as a pharmaceutical composition specifically intended to treat diseases, it can be however used for electrolyte replacement during or after profuse sweating due to a fever episode. The composition according to the present invention can also be utilized for electrolyte replacement through oral rehydration of subjects at risk of extensive electrolyte unbalance due to severe diarrhea.

The invention accordingly comprises the features of components which will be exemplified in the examples herein and the scope will be indicated hereinafter in the claims.

DESCRIPTION OF THE PREFERRED EMBODIMENTS OF THE INVENTION

In conjunction with the studies on the medical effects of thermal mud applications on various musculoskeletal disorders, the Inventors of the present invention investigated the influence of heat on sweat composition, following a research protocol similar to the one reported by Fukumoto et al. In one thermal establishment in a major Italian thermal establishment the Inventors studied sweat samples obtained from a series of 23 normal representative subjects of both sexes (average age 58.6 years, range 38 to 67), undergoing thermal therapy (hot mud treatment) for a variety of non severe musculoskeletal conditions, ranging from post-fracture and post-trauma rehabilitation to idiopathic and osteoporosis-related back-pain conditions.

None of these subjects suffered renal, cardiac, nervous or metabolic disorders (in particular diabetes was excluded). These patients underwent the standard treatment protocol, consisting of once daily hot mud applications for 10 subsequent days. The mud used was a natural clay mixture biologically activated by means of a ripening process based on several months' exposure to running hot spring water at temperatures between 50° C. and 80° C. The applied mud packs have an initial average temperature of around 500°. The mud is applied on the trunk and on the affected part if distal, after which the subject is wrapped in several layers of cotton sheet for at least 30 minutes, during which profuse sweating will typically appear. From all subjects sweat samples were collected, by means of polythene cups applied to the side of the forehead, for at least 10 minutes during the central part of the treatment session. Typically between 1 and 5 ml of transpiration fluid was collected from each subject.

A further series of 19 subjects (average age 40.3 years, range 32 to 52) did not undergo mud baths, but submitted to outside swimming and sunbathing in the same establishments where the thermal therapy was administered. Sweat samples were collected similarly from these subjects after a morning of leisure sunbathing at the hottest time of the day.

Analyses of the single sweat samples were performed as described by Fukumoto et al. (cited hereinabove) and by Hohnadel et al., *Atomic Absorption Spectrometry of Nickel, Copper Zinc, and Lead in Sweat Collected from Healthy Subjects During Sauna Bathing*, Clinical Chemistry 19(11): 1288–1292, (1973).

Though lacking an experimental group which engaged in physical exercise, a typical profile for passive heat-induced sweat emerged from experimental data, as will be summarized as follows:

Electrolyte excretion was significant in all samples, but sodium losses were consistently lower than the values reported by Fukumoto et al. (1988) for physical exercise, whereas potassium losses were more relevant, being often higher than those reported by Fukumoto et al (1988). Significant magnesium and calcium excretion was also found. Excessive losses of these elements, comprising also potassium, is deemed to significantly impair the active ion-based mechanisms involved in membrane excitability, thus negatively affecting nerve and muscle function.

Relatively high levels of excretion of zinc, copper and iron were found in passive heat conditions, confirming that sweating is an efficient mechanism for the elimination of metals, as had been claimed specifically for toxic heavy metals such as mercury and lead by Hohnadel et al. In the collected samples such toxic heavy metals were however not detected. Zinc and copper are both involved in multiple metabolic pathways, being often part of complex enzymes. Especially zinc is today viewed as an essential trace factor in skin physiology, with a protective function versus oxidation and/or UV-induced alterations of epidermal and dermal cells (Richards et al. in *Effect of Zinc Supplementation on the Resistance of Cultured Human Skin Fibroblasts Toward Xidant Stress*, Biol. Trace Elem. Res. 37 (2–3): 187–199, 1993; Record et al. In *Protection by zinc against UV-A and UV-B induced cellular and genomic damage in vitro and in vivo*, Biol. Trace Elem. Res. 53 (1–3): 19–25, 1996).

Suprisingly, traces of manganese excretion were found in the samples. The physiological significance of manganese is little understood, but it is generally regarded as an essential trace element, up to the point that it is included in traces in solutions for parenteral nutrition.

In complete accordance with previous data (Fukumoto et al., 1988), we found very consistent nitrogen excretion (urea and creatinine) in the thermal heat condition, a typical difference with physical exercise, which induces much lower nitrogen excretion levels. This may be assumed to be a specific beneficial effect of thermal treatment, comprising sauna bathing. There were no significant or consistent differences between the sweat composition of thermal therapy subjects, compared to the subjects who had undergone environmental heat stress, due to sun exposure. Our experimental data thus sustain the idea that there is indeed a difference between sweat produced in passive, resting conditions and sweat produced on strenuous exercise, and that consequently there are significant and specific differences in thirst and physiologic hydration needs between these two conditions. The physiology of the transpiration response according to inducing stimuli has been investigated by several researchers, as follows:

Nadel et al. in *Mechanisms of thermal acclimation to exercise and heat*, J. Appl. Physiol. 37 (4): 515–520, (1974) proposed a conceptual model of enhanced sweating responsiveness in the physically trained individual, as compared to the unfit individual. This would explain different sweating rates between such groups of individuals.

Henane and Bittel in *Changes of thermal balance induced by passive heating in resting man*, J. Appl. Physiol. 38 (2): 294–299, (1975) found that acclimatization to passive heating leads, after initial delays in sweating response in individual subjects, in the end to steady-state sweating rates, directly related to thermal loads applied.

Mitchell et al. in *Acclimatization in a hot, humid environment: energy exchange, body temperature, and sweating*, J. Appl. Physiol. 40 (5): 768–778, (1976) showed that physical exercise in a hot humid environment caused a wasteful overproduction of sweat, especially in the early days of acclimatization to the moist conditions.

The finding of a difference in overall sweat production rates between physical exercise and passive heat application may be taken as the key to understand our finding of a different sweat composition in the passively undergone heat stimulus. To make this clear it is necessary to refer in greater detail to the physiology of the eccrine sweat gland.

An extensive review on this subject has been given by Sato in *The Physiology, pharmacology, and biochemistry of the eccrine sweat gland*, Rev. Physiol. Biochem. Pharmacol. 79: 51–131, (1977), from which it is clear that transpiration fluid is essentially an ultrafiltrate of blood plasma, on which the sweat glands operate a selective re-uptake mechanism to avoid the excessive excretion of essential electrolytes, such as sodium. In fact, sweat is always hypotonic, as compared to blood plasma. This conservative sodium sparing mechanism is an active, energy requiring process which is fully effective when sweat is produced under heat stimulus, i.e. at the heat-induced steady-state rate, thus avoiding the excretion of too much sodium.

When sweat production is instead triggered by intensive physical exercise (endogenous vs. exogenous heat), the resulting burst of sweat overproduction apparently overcomes the capacity of the sodium re-uptake mechanism. This will result in the significantly higher sodium losses observed in exercise-induced sweat, as compared to passive heat-induced sweat. Potassium instead does not appear to benefit from any such excretion-sparing mechanism and its excretion levels are directly related to overall volume of excretion.

In the case of sodium, the essential issue lies in the time/volume rate of sweat production. Indeed, sweat is formed in two steps: production by the secretion coils of primary fluid containing nearly isotonic NaCl concentrations, followed by reabsorption of NaCl in the duct. Ductal reabsorption efficiency being critically influenced by transit time, it is the sweat rate which is the most important factor influencing final NaCl concentration in sweat. Indeed, sweat NaCl is low at the low sweat rate range, increasing to isotonicity with increasing sweat rate.

The above evidence concurs to support the notion that the hydration needs of sportsmen are different from the hydration needs of people passively undergoing the influence of environmental heat. It also supplies a rational bases for the development of a formula, specifically suitable to satisfy the electrolyte integration needs of heat-exposed individuals not engaged to any significant extent in physical exercise, with the following general characteristics, as compared to the formulas usually applied in the sports field, of the type discussed in the preamble of the present description:

reduced sodium supplementation;
increased potassium supplementation;
increased magnesium supplementation;
presence of significant levels of calcium;
presence of significant levels of zinc;
trace supplementation of manganese.

Reduced sodium supplementation is also recommended by thermal therapy specialists, in view of the mostly elderly treatment population, in whom sodium restriction is often desirable. Integration of potassium and magnesium losses had already been empirically established as essential in the acute treatment of patients in a "thermal crisis", and was therefore strongly recommended by thermal therapy specialists.

Having in mind the results coming from the analysis of the samples collected during the research campaign, the Inventors devised that a formula for restoration of electrolytic balance of persons, even young and healthy ones, subjected to environmental heat and/or sunshine had to be based mainly on reduced sodium supplementation with respect to a relative medium to high level of potassium and, possibly, magnesium. Experiments in this sense has led to identification of a preferred ratio between sodium ion and potassium ion which should not be greater than 2.5. Additionally, the ratio between sodium ion and magnesium ion should likely not exceed the value of 2.5. Applying these ratios to a rehydrating beverage led to the identification of an upper limit of about 250 mg/l of sodium ion, and a lower limit of about 100 mg/l of potassium ion and, if present, magnesium ion.

Considering the observations on the risk of early skin ageing on repeated exposure to heat, especially if in conjunction with sun or UV exposure, it was further considered appropriate to include, besides a dermotropic element such as zinc, also a significant presence of the main dermoprotective vitamins such as biotin and beta-carotene. Since the main mechanism for cutaneous tissue damage on UV exposure is free radical induction and consequent peroxidation of skin surface lipids, and also considering that the pricipal hydro-soluble antioxidant ascorbic acid had previously been implicated in heat adaption mechanisms (Strydom et al. in *Effect of ascorbic acid on rate of heat acclimatization*, J. Appl. Physiol. 41(2): 202–205, 1976), a significant presence of vitamin C appeared desirable.

The lipid peroxidation sequence induced by oxygen free radical species, such as generated by penetrating UV wavelengths, is typically interrupted by the chain-breaking mechanism provided by the lipophilic antioxidant tocopherol, acting in mutual interdependence with ascorbate (Nachbar and Kortin, *The Role of Vitamin E in Normal and Damaged Skin*, Journal of Molecular Medicine 73 (I):7–17, 1995).

Due to its lipophilic nature, the inclusion of vitamin E in aqueous solutions may present problems regarding dispersion, homogeneity and stability, even if suitable preparations have been recently effected.

As a preferred alternative, the hydro-soluble glycoside of a natural antioxidant flavonoid, Rutin (quercetin-3-rutinoside) can be included in the composition of the present invention. On intestinal absorption, Rutin is readily metabolized to yield the polyphenol quercetin. The latter compound has recently been reported to be an extremely active free radical trapper, particularly active in protecting Low Density Lipoproteins (LDL) from oxidative damage (deWhalley et al., *Flavonoids Inhibit the Oxidative Modifications of Low Density Lipoproteins by Macrophages* Biochemical Pharmacology 39(11): 1743–1750 1989; Negre-Salvayre and Salvayre, *Quercetin Prevents the Cytoxicity of Oxidized LDL on Lymphoid Cell Lines*. Free Radical Biology and Medicine 12 101–106 1992; Frankel et al. in *Inhibition of oxidation of human low-density lipoprotein by phenolic substances in red wine*, The Lancet 341: 454–457 1993). Rutin has indeed been reported to potentiate the synergistic antioxidant properties of the two main antioxidant vitamins (C and E) by NegreSalvayre et al. in *Additional antilipoperoxidant activities of alpha-tocopherol and ascorbic acid on membrane-like system are potentiated by rutin*, Pharmacology 42(S): 262–272, 1991.

On the above bases, a preferred improvement of the basic composition for the relief of heat stress as above identified may include at least significant amounts of the following additional dermoprotective-antioxidant compounds:
   ascorbate
   beta-carotene
   biotin
   rutin
   alpha-tocopherol.

Final investigations have led to the definition of the general requisites for a composition intended to integrate electrolyte losses on heat exposure, combined with suitable dermoprotective adjuncts, as follows:
sodium ion (preferentially as chloride) not more than 250 mg/L
potassium ion (preferentially as phosphate) not less than 100 mg/L
magnesium (as any nutritionally acceptable salt) not less than 100 mg/L
zinc (as any nutritionally acceptable salt) not more than 30 mg/L
manganese (as any nutritionally acceptable complex) not more than 10 mg/L
calcium (as any nutritionally acceptable salt) between 65 and 400 mg/L
vitamin C (preferentially as calcium salt) between 15 and 120 mg/L
rutin between 2.5 and 250 mg/L
biotin between 0.04 and 0.3 mg/L
beta-carotene not more than 0.45 mg
alpha-tocopherol between 2.5 and 20 mg/L On the basis of the above general formula, the following specific compositions, prepared as a beverage, powder for dispersion in water, or solid forms for oral intake, such as capsules or tablets, are presented:

Composition

| Beverage: | g/liter | preferred range |
|---|---|---|
| NaCl | 0.6 | 0.3–0.7 |
| KH$_2$PO$_4$ | 0.365 | 0.3–0.5 |
| Magnesium pidolate | 1.3 | 1.2–1.8 |
| Calcium acetate | 0.245 | 0.2–0.8 |
| Manganese pidolate | 0.003 | 0.002–0.005 |
| Zinc gluconate | 0.05 | 0.04–0.08 |
| Calcium ascorbate dihydrate | 0.035 | 0.03–0.08 |
| Rutin | 0.055 | 0025–0.25 |
| Biotin | 0.00015 | 0.00013–0.0003 |
| Beta–carotene | 0.005 | 0.004–0.03 |
| Alpha–tocopherol | 0.01 | 0.005–0.02 |

The solution, made up in deionized water, may be combined with a small amount of a non glucose carbohydrate, such as fructose or sorbitol, to give it a pleasant sweet taste, with a calorie load not exceeding 120 kcal/liter, and flavored with any choice of fruit extract and/or aroma, such as orange, lemon or others. The resulting beverage is preserved by pasteurization or sterilization and is intended for an average intake in conditions of environmental heat in amounts up to 2 liters/day.

| Powder: | Mg per dose | preferred range |
|---|---|---|
| NaCl | 150 | 50–170 |
| KH$_2$PO$_4$ | 90 | 80–150 |
| Magnesium pidolate | 330 | 300–500 |

-continued

| Powder: | Mg per dose | preferred range |
|---|---|---|
| Calcium acetate | 613 | 50–1000 |
| Manganese pidolate | 0.8 | 0.6–1 |
| Zinc gluconate | 13 | 10–20 |
| Calcium ascorbate dihydrate | 9 | 8–20 |
| Rutin | 14 | 2.5–25 |
| Biotin | 0.04 | 0.03–0.08 |
| Beta-carotene | 1.2 | 1–4 |
| Alpha-tocopherol | 2.5 | 2–8 |

The dry powder mixture is combined with a support for dispersion in water, such as mannitol, with a non-glucose sweet taste base, such as fructose or sorbitol, at a level so as not to exceed 120 kcal/L, when reconstituted, and possibly flavored with fruit extracts or aromas, such as orange, lemon, or others. One dose is intended for dissolution in 250 ml drinking water (one regular water glass). The concentrations are merely indicative, and more concentrated drinks may be prepared on the same formula basis.

Solid forms(preferably, but not exclusively, tablets)

| | mg per tablet | preferred range |
|---|---|---|
| NaCl | 10.5 | 6.0–11.0 |
| KH$_2$PO$_4$ | 10.0 | 8.0–12.0 |
| Magnesium oxide | 20.0 | 18.0–22.0 |
| Manganese gluconate | 0.4 | 0.3–0.5 |
| Zinc gluconate | 4.13 | 4.0–6.2 |
| Ascorbic acid | 1.4 | 1.3–1.8 |
| Rutin | 2.2 | 2.0–2.5 |
| Biotin | 0.006 | 0.005–0.008 |
| Beta-carotene | 0.045 | 0.04–0.06 |
| Alpha-tocopherol | 0.09 | 0.05–0.15 |

The above powder mix can be combined with a suitable support for tablet compression, with good organoleptic properties, such as sorbitol and magnesium stearate. The mass is possibly edulcorated with a known natural sweetener such as xylitol and the total energy content should not exceed 20 kcal in the average daily intake. The product may be flavored with any choice of fruit or other flavors, such as orange, lemon, menthol, eucaplytol, or the like. The compressed tablets (or equivalent solid forms with the same composition) are intended for an average daily intake of between 5 and 10 tablets.

It is also possible to provide the composition solubilized in water which is then brought in a frozen state, so as to provide—for example—flavoured ices on sticks, like the ones known under the commercial name or trade mark "Popsicle".

The above compositions are intended to give relief in conditions of sweating due to environmental heat and/or sunshine, when profuse sweating may be induced without significant physical exercise. While the composition is not intended to be a pharmaceutical composition to treat diseases induced by excessive exposure to heat or sun, the intake of the composition as described will help prevent negative consequences of heat-induced ion disturbances, without affecting the physiological thirst mechanism, and will assist in protecting from environmental heat-induced systemic effects (fatigue, exhaustion, muscle cramps, etc.).

The dermoprotective compounds included in the formulation will help prevent negative consequences of heat exposure, especially when combined with sun or UV exposure (accelerated skin ageing, UV photo damage, actinic keratosis).

The intake of the composition described is particularly useful for people submitting to thermal (hot spring water) treatment, saunas, sunbathing or UV-light exposure for tanning, and more in general, in all environmental conditions with elevated temperatures, inducing profuse sweating also in the absence of significant physical exercise. It cannot be stressed enough that the invention is not intended for the requirements of people engaging in vigorous physical exercise, but was specifically devised for the needs of people passively undergoing the potential negative effects of environmental heat or sunshine, there being very significant differences in the profile of electrolyte excretion between these two different situations.

The invention is based on extensive biomedical knowledge relating to the effects of high environmental temperatures on the human body, and may be used with positive results in multiple conditions of heat stress, which are common in many situations and climates. The following is an overview of these situations.

SAUNA—The situation which comes nearest to the thermal therapy practice originally targeted is the sauna, where elevated environmental temperature combines with a high level of moisture, to induce a pronounced sweating response. Along with an increased peripheral circulatory efficiency, the beneficial effects of the sauna also reside in the sweating response, which effectively removes accumulated waste material from the skin. A feeling of fatigue may be however more pronounced than the desired relaxation effect after a sauna and this is likely to be connected with excess electrolyte excretion. The intake of a product based on the above composition (beverage or tablets) may be therefore recommended before and after a sauna, to avoid the risk of electrolyte unbalance as a possible cause of exhaustion.

An additional aspect to be kept in mind is the external heat applied to the skin, through physical and biological (circulatory) effects, induces an acceleration of metabolic activity of the skin, again to a beneficial extent, in that renewal of skin layers is promoted. This increased metabolic activity, to be fully effective, may need to be supported by the primary vitamin involved in skin metabolic activity biotin. This essential factor for the skin is supplied in a significant amount by the preferred embodiment of the composition and increases its overall efficacy for the intended purpose of avoiding the negative effects of heat stress.

SUNBATHING (UV-TANNING)—A frequently desired feature in today's society is the exhibition of a nicely tanned skin, possible in any of the year's seasons. To this purpose many people submit to relaxing in the sun, often with a high level of exposure, or to repeated UV radiation sessions. In this situation profound effects on skin and body physiology are induced. Electrolyte losses in profuse sweating combine with potentially harmful effects of penetrating UV radiation, even up to the point that severe cutaneous inflammation (erythema or sunburn) may be acutely induced. It is indeed commonly accepted that excessive and repeated exposure to the sun or to artificial UV rays is a primary cause of premature skin ageing and degeneration, not to mention the increased risk of skin cancer. Several medical recommendations should be followed to avoid such negative effects, while still being able to enjoy the undoubtedly pleasant and beneficial effects of sun exposure, which remains essential to the human body, for instance to elaborate the factors required for normal turnover of bone tissue (vitamin D).

In this context, the intake of a nutritional product based on the composition of the present invention, particularly in its preferred embodiment, will assist in avoiding the negative effects of electrolyte losses. Since the skin ageing effect of excessive sun or UV exposure is directly connected with the oxidation sequences caused by free radicals induced in the skin by particular wavelengths present in sun and UV light, an additional beneficial effect of the present composition is conferred by the presence of antioxidant compounds, such as ascorbate and rutin.

Biotin and particularly beta-carotene, supplied in the product according to the present composition, will assist in satisfying the increased needs of the sun-exposed skin for protective factors, biotin being the primary skin vitamin and beta-carotene the skin tanning factor.

HOT CLIMATES—In today's modern society the technology of air conditioning has largely reduced the problem of the well known negative influence on human body function of high environmental temperatures. But a consistent chain of conditioned air cannot always be maintained, and a certain level of exposure to outside temperatures is often unavoidable. Less affluent and slower developing economies in geographical areas with hot climates will frequently be expoded to high temperatures, with all the negative effects, for instance when walking outside or traveling.

In these circumstances, inadvertent loss of electrolytes is common, especially in hot and dry climates (desert areas), where profuse sweating is not perceived, due to instantaneous evaporation from the skin. A severe medical condition may result, which is not resolved by simply drinking water. Fatigue and circulatory impairment is often associated with intestinal disturbances (diarrhea), and many are convinced that the latter effect is connected with poor hygiene and wrong food habits in such countries. It is however often observed that such disturbances are rarely connected with infection from food sources. It is far more likely that electrolyte unbalance at the level of intestinal mucosal membranes, where complex exchange processes take place and require continuous regulation, plays a major role in this frequent and highly disturbing effect of traveling in hot climates. The regular intake of a product based on the present composition will support the body in coping with the negative effects of the heat stress.

Apart from the importance of the composition according to the present invention to people exposed as tourists or travelers to the negative effects of environmental heat, it should be kept in mind that in the less affluent levels of society, especially among the elderly, extensive exposure to heat may occur in the summer season, even resulting in increased numbers of deaths. Body physiology in elderly people, especially in those where some level of cardiocirculatory impairment is present, is far less able to cope with the negative effects of heat stress, than in young adults. Their adaptive responses are slow and often inadequate. Food and drinking habits may be inappropriate to cope with the changed requirements of the body in response to heat. Regular use of the present composition in these people will assist in maintaining better levels of adaptive responses to heat.

WORKING ENVIRONMENT—A major goal in modern industry is to provide workers with a properly conditioned environment in which work is developed effectively and negative effects of heat on efficiency are avoided. There are however many situations in which proper conditioning cannot be guaranteed, for instance in workplaces with intensive heat sources (furnaces, baking ovens), or in otherwise unconditioned environments (trucks, trains, wagons, etc.) or directly in the open agricultural field work, construction and building). Workers in these conditions in the hot season will suffer severe heat stress with all the negative consequences on efficiency and duration of labor effort. Also cooking as a professional activity is to be included in these examples. A significant support to increase the resistance of laborers exposed extensively to high temperatures and to help them cope better with the potential negative effects, will derive from the regular intake of a product based on the Formula.

FEVER—When you run a fever, the body temperature control mechanism is upset due to the presence of an infection or other disturbing factors. The body temperature increases, not due to externally applied heat, but due to internal biological factors. The profuse sweating that is often associated with fever, especially in children, is well known. From a medical point of view a primary objective is the elimination of the infection (by prescribing antibiotics), and checking the fever (by prescribing antipyretics). An additional factor, mostly viewed as being less important from a medical point of view, is the re-establishment of an appropriate electrolyte balance, in the cases where profuse sweating has caused risk of excess electrolyte excretion. It is deemed that sweating due to endogenous heat is similar to sweating induced passively by external heat.

As a matter of fact, it is well known that sports beverages are often prescribed for this purpose. The present invention, while not being a medical treatment of the fever, may better assist to re-establish the balance of electrolytes upset due to sweating induced by endogenous heat.

Apart from the uses specifically discussed above, several other beneficial uses of the invention may be devised. Though the invention was not developed for sports purposes and is not intended to balance electrolyte losses due to heavy physical activity, there are situations of moderate exercise where beneficial effects have been suggested, for example:
  golf playing;
  mountain hiking;
  horseback riding;
  sailing and boating;
  sports fishing;

all moderate physical activities mostly associated with summertime heat and sun exposure.

We wish it understood that we do not intend to be limited to the details shown herein and other variations will occur to people skilled in the art after learning our invention.

The invention claimed is:

1. A method of replenishing electrolyte levels lowered by passive transpiration/perspiration from heat stress comprising a step of orally administering to a person in which the electrolyte levels are lowered, a liquid composition comprising from about 0.3 to about 0.7 g/liter of a sodium compound, about 0.3 to about 0.5 g/liter of a potassium compound, about 1.2 to about 1.8 g/liter of a magnesium compound, about 0.2 to about 0.8 g/liter of a calcium compound, about 0.002 to about 0.005 g/liter of a manganese compound, about 0.04 to about 0.08 g/liter of a zinc compound, about 0.025 to about 0.25 g/liter of Rutin, about 0.00013 to about 0.0003 g/liter of Biotin, about 0.004 to about 0.03 g/liter of beta-carotene and about 0.005 to about 0.002 g/liter of alpha-tocopherol, with the proviso that a carbohydrate source is not contained in the composition.

2. The method of claim 1, wherein the sodium compound is sodium chloride, the potassium compound is potassium phosphate, the magnesium compound is magnesium pidolate, the calcium compound is calcium acetate and calcium ascorbate dihydrate and the zinc compound is zinc gluconate.

3. The method of claim 1, wherein the passive transpiration/perspiration is caused by thermal therapy.

4. The method of claim 3, wherein the thermal therapy is hot mud treatment.

5. The method of claim 1, wherein the sodium ion/potassium ion ratio is no greater than 2.5.

6. The method of claim 5, wherein the sodium ion/magnesium ion ratio is no greater than 2.5.

7. A method of replenishing electrolyte levels lowered by passive transpiration/perspiration from heat stress comprising a step of administering to a person in which the electrolyte levels are or will be lowered a powder composition comprising from about 50 to about 170 mg of a sodium compound; from about 80 to about 150 mg of a potassium compound; from about 300 to about 500 mg of a magnesium compound; from about 50 to about 1,000 mg of a calcium compound; from about 0.6 to about 1 mg of a manganese compound; from about 10 mg to about 20 mg of a zinc compound; from about 2.5 to about 25 mg of Rutin; from about 0.03 to about 0.08 mg of Biotin; from about 1 to about 4 mg of beta-carotene; and from about 2 mg to about 8 mg alpha-tocopherol, with the proviso that a carbohydrate source is not contained in the composition.

8. The method of claim 7, wherein the sodium compound is sodium chloride, the potassium compound is potassium phosphate, the magnesium compound is magnesium pidolate, the calcium compound is calcium acetate and calcium ascorbate dihydrate, and the zinc compound is zinc gluconate.

9. A method of replenishing electrolytes lost by passive transpiration/perspiration from heat stress comprising a step of administering to a person in which the electrolyte levels are or will be lowered a unitary solid composition comprising from about 6 to about 11 mg of a sodium compound; from about 8 to about 12 mg of a potassium compound; from about 18 to about 22 mg of a magnesium compound; from about 0.3 to about 0.5 mg of a manganese compound; from about 4.0 to about 6.2 mg of a zinc compound; from about 1.3 to about 1.8 mg of vitamin C; from about 2.0 to about 2.5 mg of Rutin; from about 0.005 to about 0.008 mg of Biotin; from about 0.04 to about 0.06 mg of beta-carotene; and from about 0.05 to about 0.15 mg alpha-tocopherol, with the proviso that a carbohydrate source is not contained in the composition.

10. The method of claim 9, wherein the sodium compound is sodium, the potassium compound is potassium phosphate, the magnesium compound is magnesium oxide, and the zinc compound is zinc gluconate.

* * * * *